United States Patent
Littlefield et al.

(10) Patent No.: US 11,844,380 B2
(45) Date of Patent: Dec. 19, 2023

(54) PEDIATRIC HEAD COVERING FOR USE WITH THREE-DIMENSIONAL IMAGING

(71) Applicant: CRANIAL TECHNOLOGIES, INC., Tempe, AZ (US)

(72) Inventors: Timothy R Littlefield, Phoenix, AZ (US); Mary McGuire, Chicago, IL (US)

(73) Assignee: CRANIAL TECHNOLOGIES, INC., Tempe, AZ (US)

( * ) Notice: Subject to any disclaimer, the term of this patent is extended or adjusted under 35 U.S.C. 154(b) by 377 days.

(21) Appl. No.: 17/314,312

(22) Filed: May 7, 2021

(65) Prior Publication Data
US 2022/0354193 A1    Nov. 10, 2022

(51) Int. Cl.
  *A61B 5/107*      (2006.01)
  *A41D 11/00*      (2006.01)
      (Continued)

(52) U.S. Cl.
  CPC .............. *A41D 11/00* (2013.01); *A42B 1/019* (2021.01); *A42B 1/04* (2013.01); *A61B 6/032* (2013.01);
      (Continued)

(58) Field of Classification Search
  CPC ........... A41D 11/00; A42B 1/019; A42B 1/04; A61B 6/032; A61B 6/466; A61B 6/5205; A61B 2503/04; A61B 5/1077; A61B 5/1079; A61F 5/05883; G06N 20/00; G01B 21/02
  See application file for complete search history.

(56) References Cited

U.S. PATENT DOCUMENTS

| | | | | |
|---|---|---|---|---|
| 955,562 A | * | 4/1910 | Thomas | A45D 44/22 606/204.35 |
| 1,139,675 A | * | 5/1915 | Harris et al. | A42B 1/049 2/203 |

(Continued)

OTHER PUBLICATIONS

Stockinet. (n.d.) American Heritage® Dictionary of the English Language, Fifth Edition. (2011). Retrieved Jul. 18, 2023 from https://www.thefreedictionary.com/stockinet (Year: 2011).*

*Primary Examiner* — Robert H Muromoto, Jr.
(74) *Attorney, Agent, or Firm* — Donald J Lenkszus

(57) ABSTRACT

A pediatric head covering to facilitate obtaining three-dimensional images of a head of an infant to be utilized in manufacture of a cranial remodeling orthosis for correction of an abnormal head shape comprises sheer elastic material to be drawn down over an infant's head to compress the hair of an infant and to provide a smooth surface over the infant's cranium. The elastic material has variable elasticity with less elasticity over the crown of the cranium to provide enough strength to compress the infant's hair and conform to the shape of the cranium and more elasticity at the infant's neck to control soft tissue of the infant's neck without leading to distortion of the soft tissue and causing misrepresentations of the actual neck shape in captured three-dimensional images. The head covering facilitates accurate capture and reproduction of three-dimensional images of the infant's head by a three-dimensional image capturing system. The head covering is sized based upon anthropometric data derived from three-dimensional data sets of infant heads.

20 Claims, 5 Drawing Sheets

US 11,844,380 B2

Page 2

(51) Int. Cl.
*A61B 6/00* (2006.01)
*A61B 6/03* (2006.01)
*G06N 20/00* (2019.01)
*A42B 1/019* (2021.01)
*A42B 1/04* (2021.01)
*A61F 5/058* (2006.01)
*G06T 15/00* (2011.01)

(52) U.S. Cl.
CPC ............ *A61B 6/466* (2013.01); *A61B 6/5205* (2013.01); *A61F 5/05883* (2013.01); *G06N 20/00* (2019.01); *A61B 2503/04* (2013.01)

(56) References Cited

U.S. PATENT DOCUMENTS

| | | | | |
|---|---|---|---|---|
| 1,364,104 A * | 1/1921 | Geer | ...................... | A62B 18/00 128/207.11 |
| 1,395,835 A * | 11/1921 | Kops | .................... | A62B 18/082 128/206.23 |
| 1,395,836 A * | 11/1921 | Kops | .................... | A62B 18/02 128/206.28 |
| 1,395,837 A * | 11/1921 | Kops | .................... | A62B 18/02 128/206.24 |
| 1,618,222 A * | 2/1927 | Phillips | ................ | A42B 1/0186 2/172 |
| 1,898,954 A * | 2/1933 | Gustafson | ................ | A42B 1/12 2/68 |
| 2,033,802 A * | 3/1936 | Abram | .................... | A42B 1/12 2/68 |
| 2,234,546 A * | 3/1941 | Basch | .................... | A41B 13/005 2/84 |
| 2,290,885 A * | 7/1942 | Lehmberg | .......... | A41D 13/1192 128/206.16 |
| 2,458,580 A * | 1/1949 | Fisketti | .................. | A41D 13/11 128/206.13 |
| 3,026,526 A * | 3/1962 | Montrose | ................. | A42B 1/12 2/68 |
| 3,113,319 A * | 12/1963 | Vail | .......................... | A42B 1/12 2/68 |
| 3,307,202 A * | 3/1967 | Schuessler | ............... | A42B 1/06 2/173 |
| 3,872,516 A * | 3/1975 | Bird | ....................... | A42B 1/045 2/202 |
| 3,943,575 A * | 3/1976 | Bolker | .................... | A42B 1/046 2/205 |
| 3,968,521 A * | 7/1976 | Bashlow | ................ | A42B 1/046 2/203 |
| 4,281,417 A * | 8/1981 | Valentine | ................. | A42B 1/12 2/68 |
| 4,572,173 A * | 2/1986 | Comeau | .................. | A61B 46/00 2/202 |
| 5,007,115 A * | 4/1991 | Denbow | ................. | A41D 23/00 2/202 |
| 5,038,047 A * | 8/1991 | Still | .......................... | G21F 3/02 128/857 |
| 5,211,668 A * | 5/1993 | Secord | ................... | A42B 1/046 2/202 |
| 5,349,702 A * | 9/1994 | Runckel | .................. | A42B 1/12 2/DIG. 10 |
| 5,452,712 A * | 9/1995 | Richardson | ............. | A62B 17/04 128/201.28 |
| 5,621,920 A * | 4/1997 | Gorsuch | ............. | A42B 1/0186 2/195.8 |
| 5,822,800 A * | 10/1998 | Anderson | ............... | A42B 1/06 2/202 |
| 6,088,838 A * | 7/2000 | Sontag | .................. | A42B 1/046 2/202 |
| 6,397,395 B1 * | 6/2002 | DeHart | .................. | A41D 3/005 2/202 |
| 6,442,763 B1 * | 9/2002 | Larson | ................... | A42B 1/046 2/202 |
| 6,512,159 B1 * | 1/2003 | Shesol | ................... | A61F 13/122 602/41 |
| 7,096,511 B2 * | 8/2006 | Cohen | ................... | A41D 23/00 2/206 |
| D558,956 S * | 1/2008 | Pritchett | ...................... | D2/878 |
| 7,430,312 B2 * | 9/2008 | Gu | ..................... | G01B 11/2545 348/42 |
| 7,603,724 B2 * | 10/2009 | Mickle | ................... | A42B 1/046 2/202 |
| 7,744,640 B1 * | 6/2010 | Faries, Jr. | ............... | A61F 7/007 607/108 |
| D722,744 S * | 2/2015 | Brown | .......................... | D2/866 |
| 9,402,769 B1 * | 8/2016 | Hudson | .................. | A61F 11/14 |
| 9,462,839 B1 * | 10/2016 | Eppler, Jr. | ........... | G08B 21/182 |
| 9,538,799 B2 * | 1/2017 | Dodd | ........................ | A42B 1/12 |
| 9,743,068 B2 * | 8/2017 | Littlefield | .............. | H04N 23/56 |
| D831,220 S * | 10/2018 | Chase | ......................... | D24/189 |
| 10,159,296 B2 * | 12/2018 | Pietrzak | ................. | A42C 2/007 |
| 10,740,985 B2 * | 8/2020 | Sommerlade | ........... | G06T 7/337 |
| 10,780,338 B1 * | 9/2020 | Bologna | ................. | A42B 3/283 |
| 10,863,787 B2 * | 12/2020 | Chen | ..................... | A41D 13/1153 |
| 10,912,648 B2 * | 2/2021 | Gordon | .................. | B33Y 50/00 |
| 10,912,910 B1 * | 2/2021 | Yezerski | ................. | A61F 9/04 |
| 11,202,925 B1 * | 12/2021 | Awad | ..................... | A62B 7/10 |
| 11,412,787 B1 * | 8/2022 | Galustyants | ............. | A41D 1/04 |
| 11,504,256 B2 * | 11/2022 | Solce | ..................... | A42B 1/041 |
| 11,528,950 B1 * | 12/2022 | Abood | .................... | A61B 5/01 |
| 2003/0046748 A1 * | 3/2003 | Tanenbaum | ........ | A41D 19/0089 2/209.13 |
| 2004/0138729 A1 * | 7/2004 | Ladmer | ..................... | A61F 7/02 607/109 |
| 2004/0139531 A1 * | 7/2004 | Moore, III | .......... | B29C 44/1204 2/410 |
| 2004/0179728 A1 * | 9/2004 | Littlefield | .............. | B33Y 80/00 382/154 |
| 2004/0197016 A1 * | 10/2004 | Littlefield | .............. | G01N 29/28 382/128 |
| 2004/0228519 A1 * | 11/2004 | Littlefield | ............... | G06T 17/10 382/128 |
| 2004/0230149 A1 * | 11/2004 | Littlefield | .............. | A61F 5/3707 602/17 |
| 2004/0230545 A1 * | 11/2004 | Littlefield | .............. | G06T 1/0007 703/11 |
| 2004/0236708 A1 * | 11/2004 | Littlefield | .............. | B33Y 80/00 706/16 |
| 2006/0248633 A1 * | 11/2006 | Marini | ..................... | A42C 5/04 2/468 |
| 2007/0027826 A1 * | 2/2007 | Littlefield | ............... | G06T 19/20 706/16 |
| 2007/0033707 A1 * | 2/2007 | Stone | ...................... | A42B 1/06 2/209 |
| 2008/0216211 A1 * | 9/2008 | Dolby | ..................... | A42B 1/06 2/209 |
| 2010/0238273 A1 * | 9/2010 | Luisi | .................... | H04N 13/243 396/419 |
| 2010/0239135 A1 * | 9/2010 | Luisi | .................... | F16M 11/041 382/128 |
| 2010/0299807 A1 * | 12/2010 | Saito | ..................... | A42B 1/041 2/174 |
| 2012/0110828 A1 * | 5/2012 | Luisi | .................... | A61F 5/05891 29/592 |
| 2012/0113116 A1 * | 5/2012 | Luisi | ..................... | G06T 17/30 345/423 |
| 2012/0114201 A1 * | 5/2012 | Luisi | ..................... | G06V 10/772 382/128 |
| 2012/0114223 A1 * | 5/2012 | Luisi | ......................... | G06T 7/73 382/154 |
| 2012/0163901 A1 * | 6/2012 | Luisi | ..................... | B43L 13/00 401/260 |
| 2013/0033482 A1 * | 2/2013 | Luisi | ..................... | G06T 17/10 345/419 |
| 2013/0063550 A1 * | 3/2013 | Ritchey | ................. | G03H 1/2294 345/207 |
| 2013/0110415 A1 * | 5/2013 | Davis | ................... | A61B 5/6803 702/41 |

(56) References Cited

U.S. PATENT DOCUMENTS

| | | | | |
|---|---|---|---|---|
| 2013/0291272 A1* | 11/2013 | Bourque | ............ | A41D 13/1161 2/9 |
| 2014/0116456 A1* | 5/2014 | Palmer-Rogers | .... | A41G 3/0041 132/53 |
| 2014/0304887 A1* | 10/2014 | Ilges | ........................ | A42B 1/06 2/172 |
| 2014/0318565 A1* | 10/2014 | Ito | .......................... | A45D 44/22 132/319 |
| 2014/0338677 A1* | 11/2014 | Sparkuhl | ............... | A61M 16/06 128/857 |
| 2014/0373278 A1* | 12/2014 | Scott | ..................... | A61F 5/3707 5/640 |
| 2015/0113711 A1* | 4/2015 | Kim | ....................... | A42B 1/205 2/424 |
| 2015/0297397 A1* | 10/2015 | Rand | ........................ | A61F 7/02 607/110 |
| 2015/0335086 A1* | 11/2015 | Murphy | ................. | A42B 1/041 2/171 |
| 2016/0151976 A1* | 6/2016 | Littlefield | ............. | B29C 64/393 700/98 |
| 2016/0184100 A1* | 6/2016 | Joganic | ..................... | A61F 2/50 623/17.19 |
| 2016/0185046 A1* | 6/2016 | Littlefield | ............... | B29C 64/10 703/1 |
| 2016/0191900 A1* | 6/2016 | Littlefield | ................. | G06T 7/00 348/48 |
| 2017/0261416 A1* | 9/2017 | Wu | ........................ | G01M 7/00 |
| 2018/0214311 A1* | 8/2018 | Kimock | ................. | B05D 3/007 |
| 2018/0280186 A1* | 10/2018 | Littlefield | ............. | B33Y 80/00 |
| 2018/0280187 A1* | 10/2018 | Littlefield | ............. | B33Y 80/00 |
| 2018/0280188 A1* | 10/2018 | Littlefield | ............. | A63B 71/10 |
| 2018/0281312 A1* | 10/2018 | Littlefield | ............. | G06T 17/10 |
| 2018/0281313 A1* | 10/2018 | Littlefield | ............. | B33Y 50/02 |
| 2018/0281314 A1* | 10/2018 | Littlefield | ............. | B33Y 80/00 |
| 2018/0281315 A1* | 10/2018 | Littlefield | ............. | B33Y 50/02 |
| 2018/0286118 A1* | 10/2018 | Littlefield | ............. | B33Y 50/02 |
| 2019/0336330 A1* | 11/2019 | Hickey | ..................... | A61F 7/10 |
| 2020/0000644 A1* | 1/2020 | Kastros | ................. | A42B 1/012 |
| 2020/0289325 A1* | 9/2020 | Kimock | ........... | A61M 16/0683 |

\* cited by examiner

PEDIATRIC HEAD COVERING FOR USE WITH THREE-DIMENSIONAL IMAGING

FIELD OF THE INVENTION

The present invention relates to cranial remodeling of deformed shapes of infant heads, in general, and to pediatric head coverings specifically wearable by infants to facilitate three-dimensional image capture of infant heads for manufacture of custom cranial remodeling devices, in particular.

BACKGROUND OF THE INVENTION

Infants may be born with or acquire cranial deformities such as plagiocephaly. Such cranial deformities may be non-invasively treated through the use of cranial remodeling devices that are worn by an infant. As the infant grows, the cranial remodeling device causes the cranium to grow into a corrected shape. Typically infants between the ages of three through eighteen months may be treated with custom cranial remodeling devices.

Cranial Technologies, Inc. (CTI), the assignee of the present invention has been the leading developer and supplier of cranial remodeling devices for infants born with cranial deformities such as, e.g. plagiocephaly. CTI has developed systems and apparatus for capturing three-dimensional images of infants that have cranial deformities. The systems and apparatus capture highly accurate images of infants' heads and process the three-dimensional images to manufacture custom cranial remodeling orthosis devices.

Part of CTI's system and apparatus includes a computer processing programs that automates repetitive tasks performed in captured image processing such as cropping, cleaning, orienting, identifying landmarks on the cranium, manipulation of shape, generating images and generating measurements. The accuracy and speed at which the processing can occur is dependent on the accuracy of the images captured of an infant. The computer processing program utilizes machine learning. It is important for effective and efficient machine learning that the three-dimensional image shape is accurate.

Three-dimensional images of infant's head may include misrepresentations that are introduced by an infant's hair. Such misrepresentations may require system operator intervention in processing the captured three-dimensional images.

To reduce or eliminate the misrepresentations in captured images, we have determined that it is desirable to provide elastic pediatric headwear that is drawn down over an infant patient's head to maintain the hair tightly against the infant's head.

We have further determined that the headwear be such that certain landmarks on an infant's head can be identified by a clinician viewing the three-dimensional images of an infant and also automatically identifiable and utilizable by computer processing programs for data collection and calculated measurements to facilitate manufacture of a custom cranial remodeling device.

We have attempted to find commercially available pediatric headwear suitable for use in capturing accurate three-dimensional images of infant heads. No such pediatric headwear has been identified that is suitable.

We have identified adult sized headwear that may be utilized. However, There are significant problems in utilizing such commercially available adult sized headwear on infants including resulting inaccuracies in captured three-dimensional images.

The adult sized headwear identified is for different intended uses which explains some of the problems.

Such adult headwear includes wig caps for securing wigs to heads, wave caps, or interfaces to be worn between an adult user's head and a helmet to control sweating or for hygienic purposes. None of which is suitable for pediatric use to provide for accurate image capture.

One problem with adult commercially available headwear is that the size is not appropriate for pediatric use. Typically such headwear is too big with the result that the headwear is loose, long, and bunches up at the base of an infant's neck.

Conversely, in other cases, commercially available adult headwear is tight and difficult to pull over the head. This is because of the type of infant cranial deformity we treat. Many infants have heads that are deformed to be wider than adult heads.

Pediatric headwear that is commercially available is typically of the type that serves as an interface between the infant's head and a cranial device.

Additional pediatric headwear that is commercially available for use as an interface in plaster casting or for use in obtaining images of an infant's cranium utilizes hook and loop fastened chin straps that can result in misrepresenting the actual shape of the infant's head and neck in the resultant three-dimensional images.

It would be highly desirable to provide a pediatric head covering for infants to facilitate obtaining three-dimensional images of a head of an infant to be utilized in manufacture of a cranial remodeling orthosis for correction of an abnormal head shape.

It is highly desirable provide a pediatric head covering that conforms to an infant's head, compressing whatever hair may be present.

One of many objectives of the present invention is to provide a pediatric head covering for infants aged three through eighteen months that compresses whatever hair may be present on an infant's head without distorting soft tissue on the head and neck of an infant resulting in misrepresentations in captured three-dimensional images.

Another objective of the many objectives of the present invention is to provide a pediatric head covering for infants that enhances the ability of a three-dimensional image capturing system to capture an accurate image of the cranial shape of an infant's head including critical soft tissue of the neck and face of the infant.

SUMMARY OF THE INVENTION

In one embodiment, a pediatric head covering to facilitate a three-dimensional image capturing system to obtain and process three-dimensional digital images of a head of an infant of 3 to 18 months of age is provided. The head covering is sized based upon anthropometric data derived from three-dimensional data sets of a plurality of infants' heads. Each data set of anthropometric data may comprise infant head length, width, and circumference. The pediatric head covering comprises elastic material configured to be drawn down over the crown of the infant's head to cover the entirety of the head and the infant's neck. The elastic material has a variation of elasticity over its length, with less elasticity over the crown of the infant's head and more elasticity on the neck. The elasticity over the crown is selected to compress hair of the infant and to provide a smooth surface conforming to the cranium that does not misrepresent the perceived shape of the cranium to thereby permit the three-dimensional image capturing system to capture an accurate three-dimensional image of the infant's head. The three-dimensional image may be processed by an image processing system that uses machine learning.

The elastic material engages and controls soft tissue of the infant's neck without leading to distortion of the soft tissue of the neck shape.

The elastic material comprises a face opening for the infant's face. The face opening is sized to permit identification of predetermined anthropometric landmarks on the infant's face. The predetermined anthropometric landmarks are utilized for obtaining predetermined measurements.

The elastic material is configured so the opening does not produce distortion of soft tissue of the infant's face resulting in misrepresentations of the actual shape of the face.

In the embodiment, the elastic material may comprise stockinet material.

In the embodiment, the elastic material has sheerness permitting certain anthropometric landmarks to be visible through the elastic material.

In the embodiment, the face opening may frame the front of the face and sit above eyebrows of the face, clearing each outer corner of said eyebrows.

In the embodiment, the face opening may extend downward under the infant's chin.

In the embodiment, the face opening is sized to that predetermined anthropometric landmarks on the head may be accurately identified in three-dimensional images of the infant's head.

In the embodiment, the elastic material is selected to have sheerness such that ears of the infant are visible through the elastic material.

In the embodiment, the elastic material has sheerness permitting anthropometric landmarks to be visible through the elastic material.

In a second embodiment, a pediatric head covering is provided to facilitate capturing highly accurate three-dimensional digital images of a head of an infant by a three-dimensional imaging system. The imaging system processes three-dimensional images to manufacture custom cranial remodeling orthosis devices to reshape an abnormal cranium shape. The head covering comprises elastic material configured to be drawn down over the infant's head and the infant's neck to cover and conform to the entirety of the head's cranium and to provide a smooth surface over the cranium. The smooth surface is suitable for the three-dimensional image capture system to capture accurate surface data for the cranium without misrepresenting the actual shape of the cranium. In addition, the smooth surface permits capturing the surface with accuracy sufficient for a system utilizing machine learning to generate an accurate three dimensional image of the cranium. The elastic material is constructed to have less elasticity over the cranium's crown. The elasticity over the crown provides compression to compress the infant's hair that may be relatively thin or flat, or thick, or curly, or kinky and to conform to the cranium to permit the three-dimensional image capturing system to capture an accurate image of the infant's head. The head covering is sized based upon anthropometric data derived from a plurality of three-dimensional data sets of infants' heads. The anthropometric data may comprise infant head length, width, and circumference.

In the second embodiment, the elastic material is configured to engage the infant's neck with more elasticity than over the crown without distorting soft tissue of said neck resulting in a misrepresentation of the captured three-dimensional shape.

In the second embodiment, the elastic material engaging the infant's neck may extend to the base of the infant's neckline.

In the second embodiment, the elastic material may comprise stockinet material.

In the second the elastic material may be selected to have sheerness such that ears of the infant are visible through the elastic material.

In the second embodiment, a face opening may be integrally formed in the elastic material. The face opening is sized to frame the face of the infant without distorting soft tissue of the face.

In the second embodiment, the face opening may frame the front of the face. The face opening sits above eyebrows of the wearer's face and clears each corner of the infant's eyebrows.

In the second embodiment, the face opening may extend downward under the infant's chin.

In the second embodiment, the face opening may be sized so that predetermined anthropometric landmarks on an infant's head may be accurately identified in three-dimensional images of the infant's head.

In the second embodiment, the elastic material may be selected to have sheerness such that ears of the infant are visible through the elastic material.

In the second embodiment, the elastic material may have sheerness permitting certain anthropometric landmarks to be visible through the elastic material.

BRIEF DESCRIPTION OF THE DRAWING

The invention may be better understood from a reading of the following detailed description in conjunction with the drawing figures, in which like designators identify like elements in the various figures, and in which.

DETAILED DESCRIPTION

Figure 1:
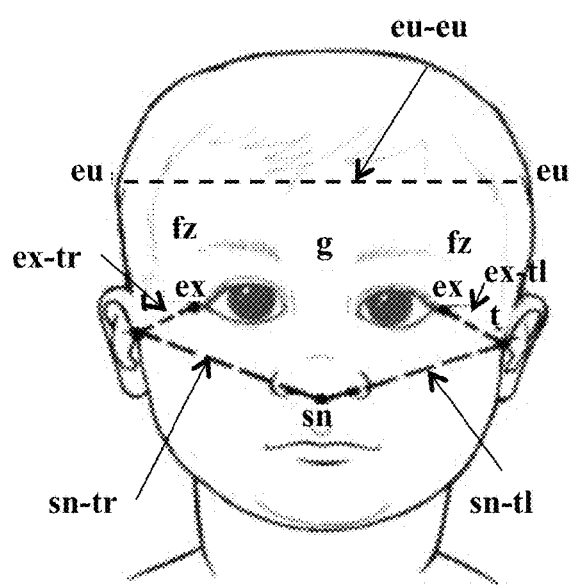
FIG. 1 is a front view image of an infant's head illustrating the location of predetermined anthropometric landmarks.
Figure 2:
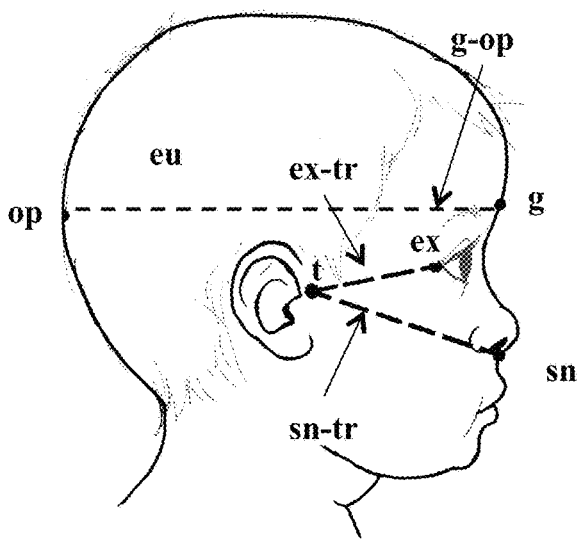
FIG. 2 is a side view image of an infant's head illustrating the location of predetermined anthropometric landmarks.

CTI has developed a three-dimensional photographic based or optical image capture system for use in capturing three-dimensional images of infants as part of a system for the manufacture of custom cranial remodeling devices for infants having cranial defects resulting in non-normal cranial shapes.

Three-dimensional image capture systems are described in patents assigned to the present assignee. Three-dimensional digital capture apparatus comprising optical capture apparatus are described in U.S. Pat. Nos. 7,142,701, 7,162, 075, 7,245,743, 7,280,682, 7,305,369, 7,542,950, 8,103,088, and 8,217,993 all of which are assigned to the assignee of this invention.

The methodology for generating head shape data files is described in the above-identified patents and additionally in U.S. Pat. Nos. 8,442,288, 8,442,308, 8,472,686, 8,494,237, and 8,787,657 all of which are assigned to the assignee of this invention. The disclosures of all the above listed patents are incorporated herein by reference.

The image capture system works in conjunction with a computer processing program that automates repetitive tasks performed in captured image processing such as cropping, cleaning, orienting, identifying landmarks on the cranium, and generating pictures and measurements. The accuracy and speed at which the processing can occur is dependent on the accuracy of the images captured of an infant.

To obtain accurate images that do not contain extraneous information such as hair, it is desirable to utilize an elastic head covering that maintains an infant's hair as close to the scalp as possible. In addition to maintaining the infant's hair close to the scalp, it is desirable to provide a head covering of an elastic fabric that is see-through or sheer such that anthropometric landmarks on the head may be determined.

Anthropometric landmarks of an infant's head are utilized by CTI's system and apparatus to generate a custom cranial remodeling device for the infant to correct for cranial abnormality. The anthropometric landmarks are used to represent the geometric shape of the infant's head and are utilized to calculate key measurements of the infant's head.

Anthropometric landmarks of interest are shown in FIGS. 1 through 5, inclusive.

Euryon eu is the most lateral point on the head located in the parietal region.

*Glabella* g that is the most prominent point in the median sagittal plane between the supraorbital ridges; viewed laterally. Ophryon on is a point, at the mid-plane, of a line tangent to the upper limits of the eyebrows. Ophryon can be used as an approximation of *glabella* g where *glabella* g is not readily apparent.

Nasion n is located at the midpoint of the nasofrontal suture. It is typically the point of inflection, i.e., deepest part of the concavity, in the bridge of the nose.

Opisthocranion op is the most prominent posterior point of the occipit.

Tragion t is located at the notch above the tragus of the ear, i.e., the cartilaginous projection in front of the external auditory canal, where the upper edge of cartilage disappears into the skin of the face.

Frontozygomaticus fz is the most lateral point on the frontozygomatic suture.

Exocanthion ex is the outer corner of the eye fissure where the eyelids meet.

Subnasale sn is the midline area under the nose, i.e., the base of the columella.

Anthropometric measurements are calculated by CTI's apparatus and system utilizing the anthropometric landmarks. The measurements may be utilized to document a plagiocephalic profile, to document effectiveness of orthotic treatment of a head shape, to help in diagnosis of positional plagiocephaly, to generate a custom orthotic device to treat an infant's cranial deformity, and to assist a machine learning system to add to its learned capabilities.

The calculated measurements provide basic information needed to evaluate the observed dominant plagiocephalic framework of the head and face, which is asymmetrical, while minimizing the risk of covariance.

Positional plagiocephaly is primarily characterized by right or left occipital flattening (vault asymmetry), with advancement of the ipsilateral ear, and a prominence of the ipsilateral frontal region (skull base asymmetry, orbito-tragial asymmetry), measurements are calculated reflecting these asymmetrical regions.

Scaphocephaly/dolichocephaly and brachycephaly may be predominantly described by calculating the maximum cranial length and maximum cranial breadth measurements and then calculating the cephalic index.

A head circumference is calculated for determining the shape of a custom cranial remodeling device.

Figure 3:
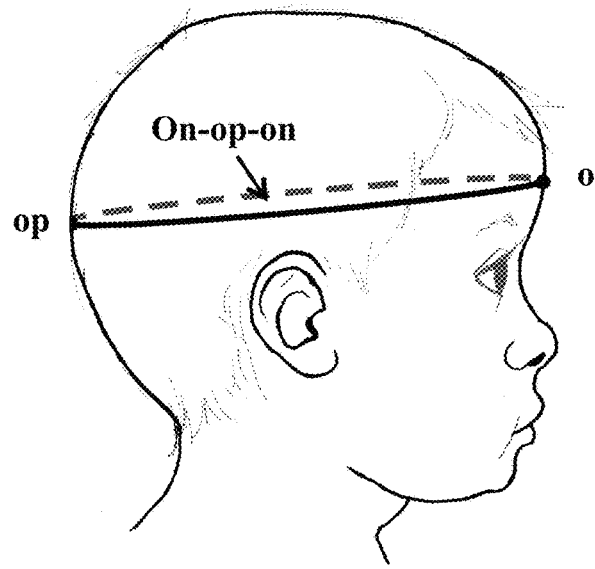
FIG. 3 is a side view image of an infant's head illustrating the location of predetermined anthropometric landmarks.

Maximum cranial length landmarks are *glabella* g and Opisthocranion op. The maximum length g-op is shown in FIG. 3.

Figure 4:
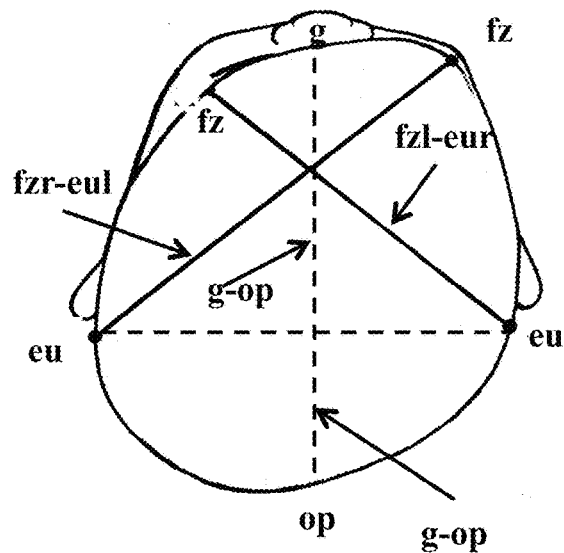
FIGS. 4 and 5 are top view images of an infant's head illustrating the location of predetermined anthropometric landmarks.

Maximum cranial breadth/width eu-eu determined from the left and right euryoneuryon eul, eur as shown in FIG. 4.

A Cephalic Index is calculated by multiplying the maximum cranial breadth/width eu-eu times 100 and dividing the result by the maximum length g-op. This index, which is a ratio of the maximum width of the skull to the maximum length is a measure of the overall shape of the skull vault. The larger the index indicates the shorter and/or wider the skull and the smaller the index indicates the longer and/or narrower the skull.

An oblique cranial length or cranial vault asymmetry is calculated using bilateral landmarks fzr, eul and contralateral landmarks fzl, eur to generate cranial lengths fzr-eul, fzl-eur as shown in FIG. 4

Figure 5:
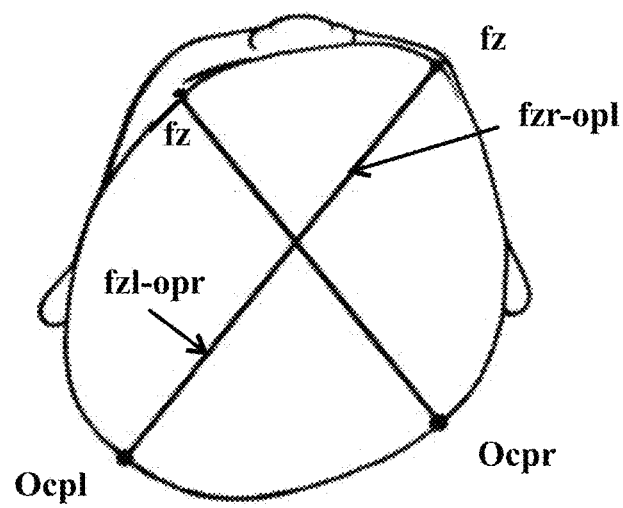

Trans Cranial Vault Asymmetry is determined by calculating bilateral frontozygomaticus-occipital prominence/flatness fzr-ocpl and contralateral frontozygomaticus-occipital prominence fzl-ocpr as shown in FIG. 5

Mid-face asymmetry is determined by calculating an orbito-tragial depth for each side ex-tl, ex-tr shown in FIG. 1 utilizing exocanthion ex and tragion t landmarks.

Skull Base Asymmetry is calculated utilizing bilateral landmarks subnasale sn and tragion t as shown in FIG. 1.

A head circumference on-op-on is calculated utilizing: ophryon on and opisthocranion op landmarks as shown in FIG. 3.

CTI's system and apparatus has the capability to automatically identify anthropometric landmarks and calculate the various measurements listed above.

It is desirable to generate trim lines for cranial remodeling devices including trim lines include framing the face above the eyebrows and down the side of the face. It is also desirable to identify proper curvature/inflection points for the upper rim and the location and length of the neck line, and location of ear contours. Ear contours are determined by identifying top ear points, bottom ear points, front ear points and back ear points.

Identification of the above-described anthropometric points is easily provided in the embodiments of the invention by utilizing a fabric for the infant sized head covering that permits anthropometric points to be visible when the head covering is in place on an infant.

Figure 6:
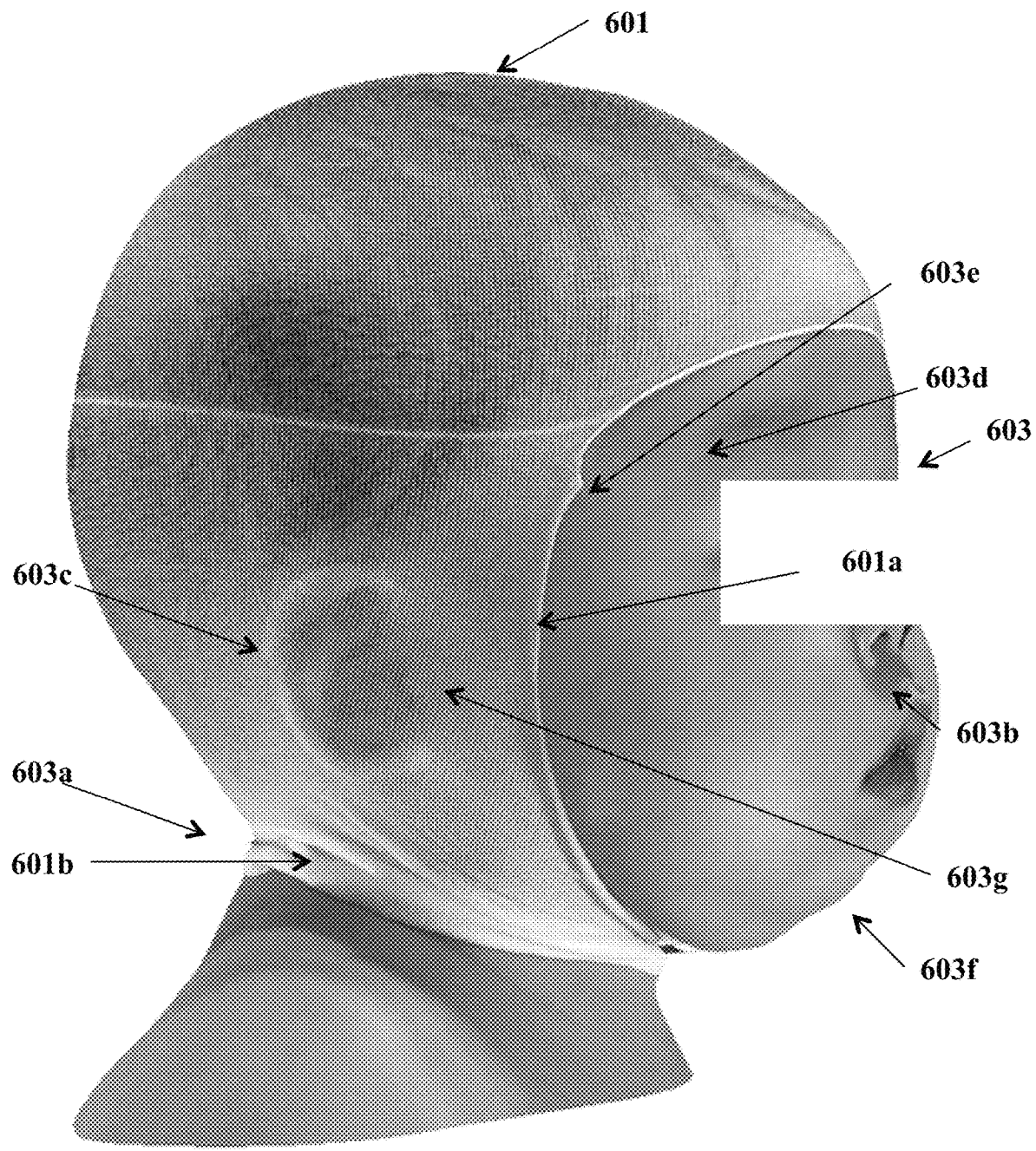
FIG. 6 is a side view photograph of an infant's head with an embodiment of a pediatric head covering with identifying features of the infant obscured.
Figure 7:
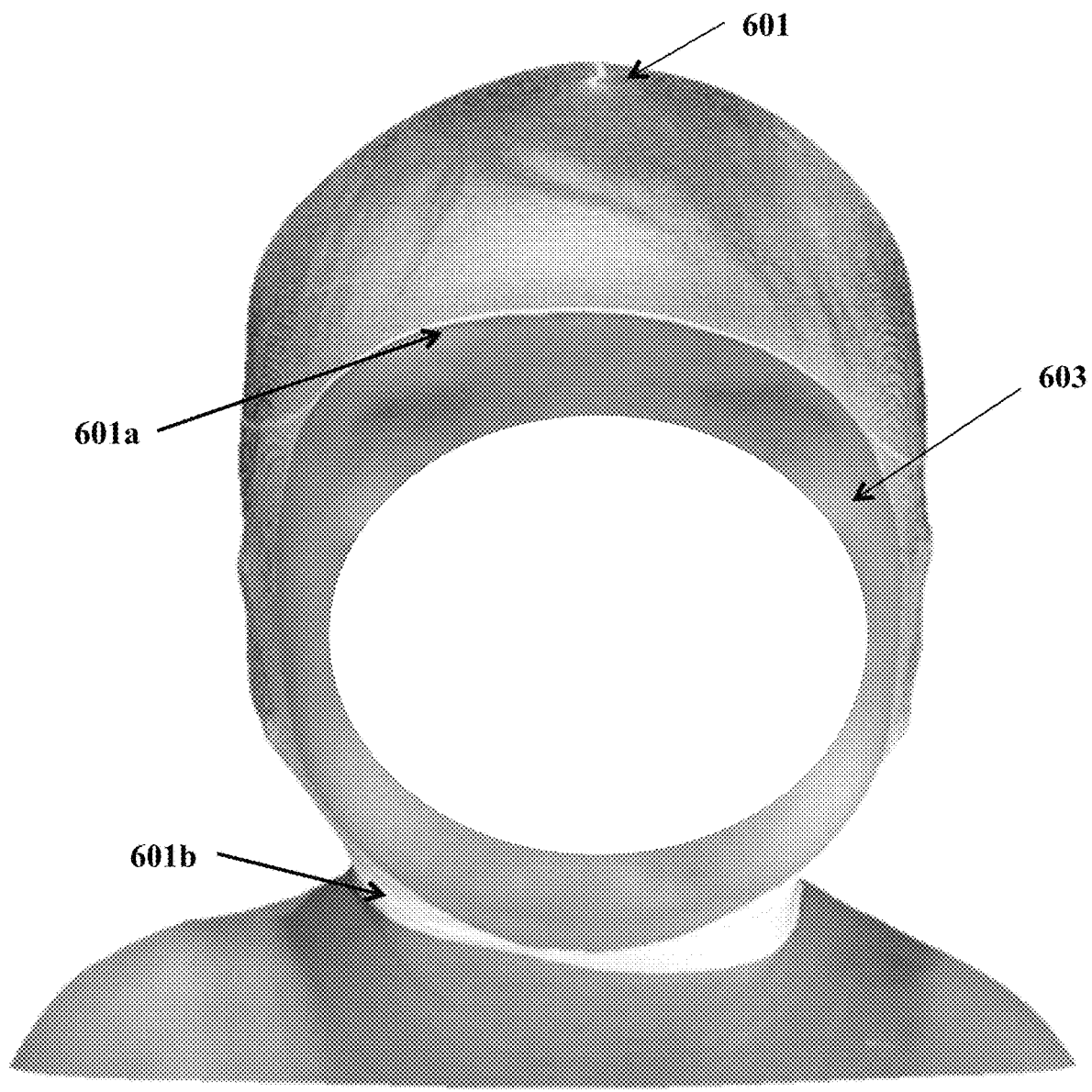
FIG. 7 is a front view photograph of the infant's head of FIG. 6 with identifying features of the infant obscured.
Figure 8:
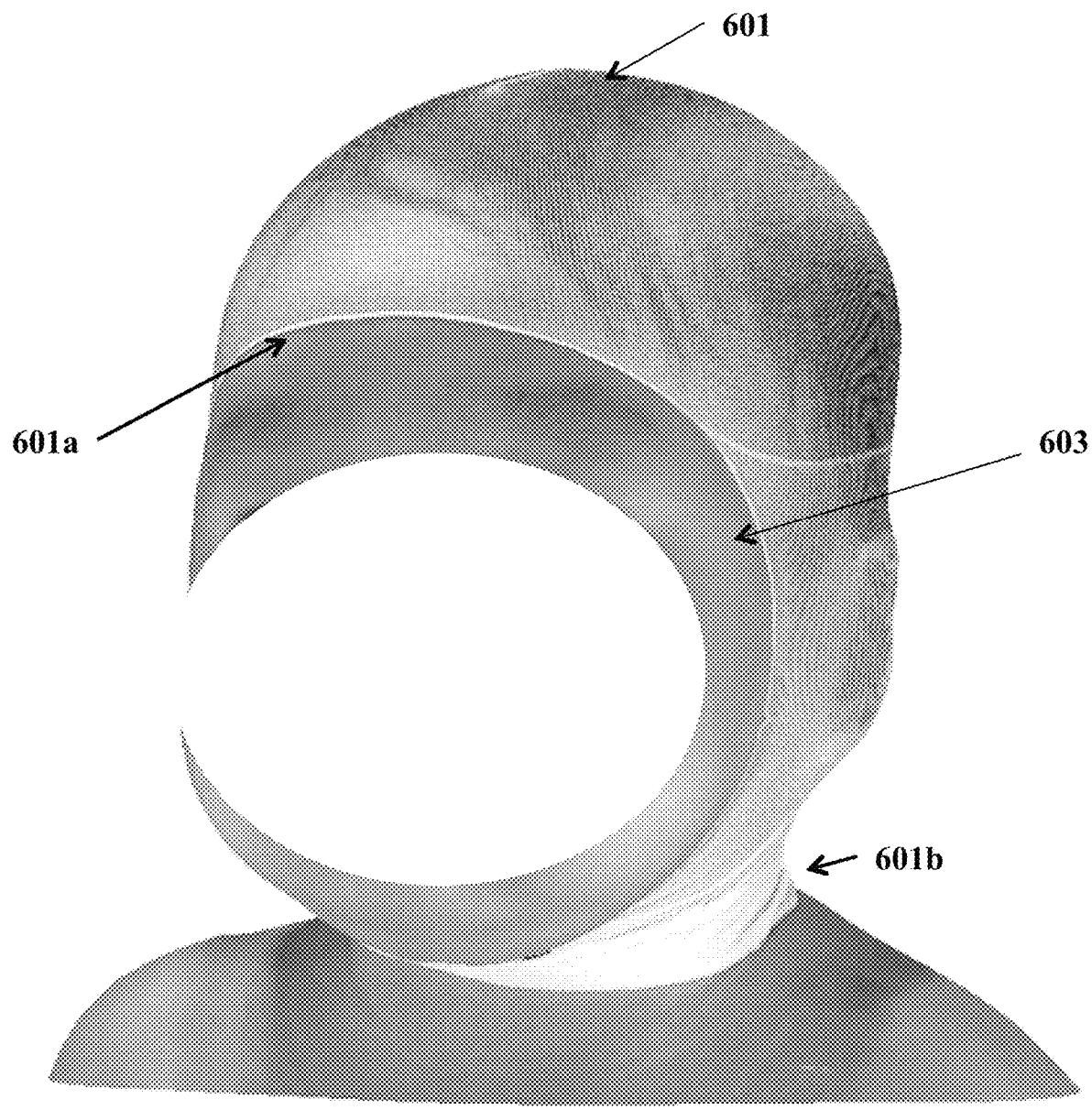
FIG. 8 is a left front view photograph of the infant's head of FIG. 6 with identifying features of the infant obscured.

Turning now to FIGS. 6, 7, and 8, an infant sized head covering 601 particularly suited for three-dimensional image capture of an infant's head 603 is shown. Pediatric headwear 601 is sized for infants and in the embodiment comprises a sheer elastic material. The sheer elastic material is selected to be such that features of the infant's head are visible through the material.

The infant sized head covering 301 facilitates obtaining three-dimensional imaging of an infant's head 603 of at least 3 to 18 months of age. When an infant is older than eighteen months custom cranial remodeling devices are typically not used to initiate treatment of cranial deformities.

Head covering 601 comprises sheer elastic material configured to cover infant's head 603. The size of head covering 601 has been determined from a database of three dimensional anthropometric data from a large number of prior infant patients each having a cranial deformity and includes cranial length, cranial width, and cranial circumference for each of the infants. The database contains anthropometric data and measurements for a large number of infants of different ages between at least the ages of three to eighteen months of age.

Head covering 601 is drawn down over the cranium of infant 603.

The sheer elastic material of head covering 601 is selected to have an elasticity of enough strength to compress the infant's hair. The sheer elastic material is also selected to compress the infant's hair without digging into soft tissue of the infant's head and misrepresenting the actual shape of the infant's head while a three-dimensional image of head 603 is captured. The sheer elastic material is configured to include a portion 601*b* to engage the infant's neck around the base of the neck 603*a* to control soft tissue of the infant's neck without leading to distortion of the soft tissue and causing misrepresentations of the actual neck shape in captured three-dimensional images.

Head covering 601 comprises an opening 601*a* for the infant's face 603*b*. Opening 601*a* is sized to permit identification of predetermined anthropometric landmarks on the infant's face 603*b*. As pointed out above, the predetermined anthropometric landmarks are utilized for obtaining predetermined measurements for the custom cranial remodeling device. The sheer elastic material of head covering 601 is configured so the facial opening 601*a* does not distort the soft tissue of infant's face 603*b*.

Face opening 601*a* frames the front of face 603*b* and sits above eyebrows 603*d* of face 603*b*, clearing each outer corner 603*e* of each eyebrow 603*d*.

Face opening 601*a* extends downward under the infant's chin 603*f*. Head covering 601 includes a portion 601*b* that engages neck 603*a*.

Face opening 601*a* is sized so that predetermined anthropometric landmarks on the head such as those shown in FIGS. 1 through 5 may be accurately identified in three-dimensional images of infant head 603.

The elastic material is selected to have sheerness such that ears 603*c* of infant 603 are visible through the elastic material to easily permit identification of the tragus 603*g* and to identify ear points.

The elastic material is further selected to have less elasticity over the crown of the head and more elasticity in the neck portion 601*b* so that the soft tissue of the neck is not distorted.

In another embodiment of the invention that is not shown, a pediatric head covering 601 to facilitate obtaining three-dimensional images of a head of an infant to be utilized in manufacture of a cranial remodeling orthosis for correction of an abnormal head shape does not include opening 601*a*. Head covering 601 comprises a unitary seamless sheer elastic material constructed to be drawn down over the head 603 to cover the entirety of the infant's cranium to provide a smooth surface over the cranium that is suitable for capture by image capture apparatus adapted to capture surface data for the cranium with an accuracy to generate a three dimensional image of infant head 603 for manufacture of a custom cranial remodeling orthosis.

As with the first embodiment, elastic material is constructed to have an elasticity to provide enough strength to compress hair of an infant without digging into soft tissue of the infant's head and misrepresenting the actual shape of said infant's head in captured three-dimensional images. This permits visualization of the infant's head's shape by a clinician, and further permits a three-dimensional image capturing system to capture an accurate three-dimensional image of infant head 603. Head covering 601 is sized is the same manner as the first embodiment.

Head covering 601 of the second embodiment comprises a sheer elastic material and includes a neck portion 601*b* configured to engage an infant's neck 603*a* without distorting soft tissue of the neck.

The sheer elastic material of the second embodiment also comprises stockinet material.

The elastic material is selected to have sheerness such that ears of an infant are visible through the elastic material to permit identification of the tragus of each ear as well as other anthropometric landmarks.

In other embodiments, the head covering may include location markers on its exterior surface that facilitate production of the three-dimensional image of an infant's head.

It will be appreciated that various changes and modifications may be made to the embodiments of the invention without departing from the spirit or scope of the invention. It is not intended that the invention be limited in scope by the embodiments shown and/or described herein. It is intended that the invention only be limited by the claims appended hereto.

The invention claimed is:

1. A pediatric head covering to facilitate a three-dimensional image capturing system to obtain and process three-dimensional digital images of a head of an infant of 3 to 18 months of age, comprising:
   elastic material configured to be drawn down over the crown of said infant's head to cover the entirety of said head and said infant's neck;
   said elastic material having less elasticity over the crown of said head and more elasticity on the entirety of said neck, said elasticity over said crown selected to compress hair of said infant and to provide a smooth surface conforming to said cranium, when worn, that does not misrepresent the perceived shape of said cranium to permit said three-dimensional image capturing system to capture an accurate three-dimensional image of said infant head, three-dimensional image being operable on by an image processing system that uses machine learning;
   said elastic material engages the entirety of said neck around the base of the neck to control soft tissue of the infant's neck without leading to distortion of the soft tissue and causing misrepresentations of the actual shape of said neck in captured three-dimensional images;
   said elastic material comprises a face opening for said infant's face, said face opening sized to permit identification of predetermined anthropometric landmarks on said infant's face, said predetermined anthropometric landmarks being utilized for obtaining predetermined measurements; and
   said elastic material configured so said opening does not produce distortion of soft tissue of said infant's face.

2. A head covering in accordance with claim 1, wherein:
   said elastic material comprises stockinet material.

3. A head covering in accordance with claim 2, wherein:
said elastic material has a sheerness permitting certain anthropometric landmarks to be visible through said elastic material.

4. A head covering in accordance with claim 1, wherein:
said face opening frames the front of said face, when worn;
said face opening sits above eyebrows of said infant face and clears each outer corner of said eyebrows.

5. A head covering in accordance with claim 4, wherein:
said face opening extends downward under said infant's chin, when worn.

6. A head covering in accordance with claim 1, wherein:
said face opening is sized to that predetermined anthropometric landmarks on said head may be accurately identified in three-dimensional images of said infant's head.

7. A head covering in accordance with claim 1, wherein:
said elastic material is selected to have sheerness such that ears of said infant are visible through said elastic material.

8. A head covering in accordance with claim 1, wherein:
said elastic material has sheerness permitting certain anthropometric landmarks to be visible through said elastic material.

9. A pediatric head covering to facilitate capturing highly accurate three-dimensional digital images of a head of an infant, said three-dimensional images to be processed to manufacture custom cranial remodeling orthosis devices to reshape said head to reshape an abnormal cranium shape, said head covering comprising:
elastic material configured to be drawn down over said head and said infant's neck and to cover and conform to the entirety of said head's cranium to provide a smooth surface over said cranium, said smooth surface being suitable for a three-dimensional image capture system to capture accurate surface data for said cranium without misrepresenting the actual shape of said cranium and to an accuracy sufficient for a system utilizing machine learning to generate an accurate three dimensional image of said cranium for manufacture of a custom cranial remodeling orthosis;
said elastic material being constructed to have less elasticity over said cranium's crown, said elasticity over said crown to provide enough strength to compress hair of said infant, when worn, and to conform to said cranium to permit said three-dimensional image capturing system to capture an accurate image of said infant head; and
said elastic material being constructed to have more elasticity over the entirety of said infant neck.

10. A head covering in accordance with claim 9, wherein:
said elastic material is configured to engage said infant's neck with more elasticity than over said crown to control soft tissue of the infant's neck without leading to distortion of the soft tissue and causing misrepresentations of the actual neck shape in captured three-dimensional images.

11. A head covering in accordance with claim 10, wherein:
said neck portion is sized to extend to the base of said infant's neckline, when worn.

12. A head covering in accordance with claim 11, wherein:
said elastic material comprises stockinet material.

13. A head covering in accordance with claim 9, wherein:
said elastic material is selected to have sheerness such that ears of said infant are visible through said elastic material.

14. A head covering in accordance with claim 9, comprising:
a face opening integrally formed in said elastic material, said face opening sized to frame the face of said infant without distorting soft tissue of said face, when worn.

15. A head covering in accordance with claim 14, wherein:
said face opening frames the front of said face, when worn, without leading to distortion of the soft tissue and causing misrepresentations of the face in captured three-dimensional images;
said face opening sits above eyebrows of said infant face and clears each corner of the infant's eyebrows, when worn.

16. A head covering in accordance with claim 15, wherein:
said face opening extends downward under the chin of said infant, when worn.

17. A head covering in accordance with claim 16 wherein:
said face opening is sized so that predetermined anthropometric landmarks on said head may be accurately identified in three dimensional images of said infant's head.

18. A head covering in accordance with claim 17, wherein:
said elastic material is selected to have sheerness such that ears of said infant are visible through said elastic material.

19. A head covering in accordance with claim 17, wherein:
said elastic material has sheerness permitting certain anthropometric landmarks to be visible through said elastic material.

20. A head covering in accordance with claim 10, wherein:
said elastic material has sheerness permitting certain anthropometric landmarks to be visible through said elastic material.

* * * * *